United States Patent
Baldi Coll et al.

(10) Patent No.: US 10,254,243 B2
(45) Date of Patent: Apr. 9, 2019

(54) ION SENSOR WITH DIFFERENTIAL MEASUREMENT

(71) Applicant: CONSEJO SUPERIOR DE INVESTIGACIONES CIENTIFICAS (CSIC), Madrid (ES)

(72) Inventors: Antonio Baldi Coll, Cerdanyola del Valles (ES); César Fernández Sánchez, Cerdanyola del Valles (ES); Alfredo Cadarso Busto, Cerdanyola del Valles (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 0 days.

(21) Appl. No.: 15/743,923

(22) PCT Filed: Jul. 12, 2016

(86) PCT No.: PCT/ES2016/070527
§ 371 (c)(1),
(2) Date: Jan. 11, 2018

(87) PCT Pub. No.: WO2017/009510
PCT Pub. Date: Jan. 19, 2017

(65) Prior Publication Data
US 2018/0209933 A1    Jul. 26, 2018

(30) Foreign Application Priority Data
Jul. 13, 2015  (ES) .................................. 201531018

(51) Int. Cl.
*G01N 27/414*  (2006.01)
*G01N 27/30*  (2006.01)

(52) U.S. Cl.
CPC ......... *G01N 27/414* (2013.01); *G01N 27/301* (2013.01)

(58) Field of Classification Search
CPC .......................... G01N 27/301; G01N 27/414
See application file for complete search history.

(56) References Cited

U.S. PATENT DOCUMENTS

| | | |
|---|---|---|
| 4,592,824 A | 6/1986 | Smith |
| 4,874,499 A | 10/1989 | Smith |

(Continued)

FOREIGN PATENT DOCUMENTS

| | | |
|---|---|---|
| EP | 0 155 725 A1 | 9/1985 |
| EP | 0155725 A1 | 9/1985 |

(Continued)

OTHER PUBLICATIONS

International Search Report and Written Opinion in corresponding PCT Application No. PCT/ES2016/070527 dated Dec. 1, 2016.
Bergveld P et al: 11 How electrical and chemical requirements for refets may coincide, Sensors and Actuators, Elsevier, Switzerland, Jul. 1989 (Jul. 1, 1989), vol. 18, No. 3-4, 1 pp. 309-327.

(Continued)

*Primary Examiner* — Yosef Gebreyesus
(74) *Attorney, Agent, or Firm* — Leason Ellis LLP

(57) ABSTRACT

The present invention concerns an ion sensor based on differential measurement, that by means of at least two ion-sensitive field-effect transistors, compares the concentration of certain ions in a solution to be measured with the concentration of certain ions in a reference solution contained in a micro-reservoir with a micro-channel. To do this, the micro-reservoir and the micro-channel cover at least the gate of one of the ion-sensitive field-effect transistors and make up a unit partially filled with a porous material that covers the entirety of the aforementioned gate and at least the base of the micro-channel.

10 Claims, 7 Drawing Sheets

(56) References Cited

U.S. PATENT DOCUMENTS

| | | | |
|---|---|---|---|
| 2009/0194417 A1 | 8/2009 | King | |
| 2011/0217697 A1* | 9/2011 | Rothberg | C12Q 1/6874 435/6.1 |
| 2014/0264464 A1* | 9/2014 | Fife | G01N 27/414 257/253 |

FOREIGN PATENT DOCUMENTS

| | | |
|---|---|---|
| NL | 8 602 669 A | 5/1988 |
| NL | 8602669 A | 5/1988 |
| WO | 0077505 A2 | 12/2000 |
| WO | WO 00/77505 A2 | 12/2000 |
| WO | WO 2015/121516 A1 | 9/2009 |
| WO | 2015121516 A1 | 8/2015 |

OTHER PUBLICATIONS

Pierre A Comte, et al., A Field Effect Transistor As a Solid-State Reference Electrode, Analytica Chimica Acta (1978), vol. 101, pp. 247-252.
Bergveld et al. "How electrical and chemical requirements for REFETs may coincide." Sensors and Actuators 18.3-4 (1989): 309-327.
Comte et al. "A field effect transistor as a solid-state reference electrode." Analytica Chimica Acta 101.2 (1978): 247-252.
International Preliminary Report on Patentability in corresponding International Patent Application No. PCT/ES2016/070527, dated Jan. 16, 2018. 7 pages.
International Search Report (Translation) in corresponding International Patent Application No. PCT/ES2016/070527, dated Dec. 1, 2016. 7 pages.

* cited by examiner

STATE OF THE ART

ION SENSOR WITH DIFFERENTIAL MEASUREMENT

CROSS-REFERENCE TO RELATED PATENT APPLICATIONS

This application is a U.S. National Phase Application under 35 U.S.C. § 371 of International Patent Application No. PCT/ES2016/070527, filed Jul. 12, 2016, and claims the priority of P 201531018, filed Jul. 13, 2015, all of which are incorporated by reference in their entireties. The International Application was published on Jan. 19, 2017 as International Publication No. WO 2017/009510 A1.

OBJECT OF THE INVENTION

The technical field of the present invention is the measurement of ions, and its more common application is the measurement of pH, i.e. the concentration of hydrogen ions in an aqueous solution.

The present invention concerns an ion sensor based on differential measurement that compares the concentration of certain ions in a solution to be measured with a reference solution contained in a micro-reservoir.

BACKGROUND OF THE INVENTION

Currently, several techniques are known for performing the measurement of ion concentrations in a medium.

One of the most used techniques is the measurement with ion-selective electrodes (ISEs). More specifically, these electrodes comprise a selective membrane that generates an electric potential by exchanging the ions in the solution with this membrane. Currently, several types of selective membranes are known, such as crystalline membranes, glass membranes, or resin membranes. To perform the measurement of the electric potential, these electrodes require an internal reference electrode, that is immersed into a reference solution, and an external electrode immersed into the solution to be measured.

Another type of widely known sensors are the ion-sensitive field-effect transistor (ISFET) sensors. These transistors are based on field-effect transistors and usually comprise three terminals: one gate, one drain and one source. More specifically, these sensors are made on integrated circuitry (chip) and comprise a reference electrode that is not integrated in the chip. This sensor varies its threshold voltage according to the ion concentration of the solution where it is immersed into; specifically, it varies its voltage according to the ions in contact with its gate. This gate is made of a membrane that is selective to at least one type of ion. So, depending on the chosen membrane, the transistor will respond to a specific type of ion. The aforementioned threshold voltage is defined as the minimum voltage difference between the reference electrode and the source required to create a current flow between the source and the drain.

Both the sensors based on ISE electrodes and the sensors based on ISFET require a reference electrode, which is not integrated in the sensor, to measure ions. Hence, they are expensive to produce and need periodic maintenance.

Finally, there is an alternative way to perform the measurement of pH that requires no reference electrodes and that includes two ISFET transistors. In particular, one of the ISFET performs the ion measurement in the solution to be measured through its gate. Meanwhile, the gate of the other ISFET, which is sensitive to pH, remains exposed to a constant pH concentration with the incorporation of a structure covering the gate as a kind of micro-reservoir. This micro-reservoir is filled with a reference solution, which is a buffer solution at a specific pH level, and is connected to the outside, i.e. with the solution to be measured, by a micro-channel through which a liquid junction between the two solutions occurs. In this way, we obtain a reference ISFET transistor, commonly known as REFET.

Specifically, the aforementioned liquid junction allows a small potential difference between the solution to be measured and the reference solution, and thus the differential measurement of the ISFET and REFET depends chiefly on the response of the ISFET to pH or on the concentration of other ions in the solution to be measured.

A known example of this embodiment consists on the formation of a micro-reservoir sealed with an epoxy resin containing directly the reference solution, or containing a gel that has previously absorbed this reference solution. This micro-reservoir allows the reference solution to keep in contact with the REFET gate. Additionally, a glass capillary tube allows the contact between the reference solution and the solution to be measured.

The problem with this type of sensors is its useful life, as it depends on the volume of the micro-reservoir and the volume of the micro-channel. This is due to the fact that the reference solution in the micro-reservoir will be diluted and/or contaminated through the micro-channel, and so the error in the measurement will increase progressively as the pH level inside the micro-reservoir is no longer properly buffered and varies more strikingly during the performance of the measurement. For this reason it is considered a sensor with short useful life.

Another problem with this type of sensor is that when it is stored in a dry environment for a long period of time, the reference solution in the micro-reservoir evaporates slowly through the micro-channel and is replaced by air. Consequently, either the reference solution evaporates completely or air bubbles appear in the reference solution when the sensor is immersed again into the solution to be measured, hampering the sensor to work properly. For example, if the air bubbles remain in the surface of the REFET gate, or if they jam in the micro-channel obstructing the liquid junction between the outside and the inside of the micro-reservoir, the measurement of the sensor will be incorrect.

To solve these problems, there is another type of ISFET-REFET differential sensor which allows the renewal of the reference solution contained in the micro-reservoir. To that end, the micro-reservoir and the micro-channel of this sensor are fully filled with a gel coating the ISFET gate that makes up the REFET. This configuration prevents the formation of air bubbles in the micro-channel and in the micro-reservoir, and hence it avoids this problem of malfunctioning. Besides, this ISFET-REFET differential sensor allows being stored dry until its first use, or after several uses.

More specifically, the gel is soaked with the reference solution, into which the sensor has been previously immersed, and does the same function as if it contained the reference solution directly, but avoiding the formation of air bubbles in the REFET gate or in the micro-channel, hereinafter referred to as "REFET gate".

That is, this ISFET-REFET sensor comprises a gel to contain the reference solution inside the micro-reservoir and the micro-channel with the aim of preventing problems with air bubbles and allowing a quick rehydration if the gel gets dry.

In particular, this type of sensor, for its correct use, must be first immersed into a reference solution so that the gel can absorb it. Once the REFET is filled with the solution, the calibration can be made in the same reference solution. After this step, measurements are performed to compare the ion concentration in the solution to be measured with the ion concentration in the reference solution. Subsequently, if needed, the sensor can be immersed again into the reference solution of the same type for calibrating again the sensor and for allowing the solution in the micro-reservoir, which may have varied slightly during the measurement, to renew by diffusion through the channel.

Despite these advantages, this sensor presents a significant error in the measurement of electric potential. This is due to the fact that additional potential arises between the REFET gate and the ISFET gate. Specifically, this potential arises between the gel and the external solution to be measured. The said potential, known as Donnan potential, which depends on the concentration of the different ions in the solution to be measured, causes an interference in the measurement, and thus reduces the sensor's accuracy.

The abovementioned interferences are evidenced in FIG. 1a and FIG. 1b, where two ISFET-REFET differential sensors have been immersed into two buffer solutions with pH 7 and pH 4. In particular, FIG. 1a shows the results obtained with a REFET the micro-reservoir and micro-channel of which are totally filled with poly(HEMA)-type gel, and which has been previously soaked with a buffer solution with pH 7. In contrast, FIG. 1b shows the results obtained with a REFET the micro-reservoir and micro-channel of which are totally filled with the buffer solution with pH 7.

To apply the gate voltage of both REFETs, a reference electrode has been used in order to ensure variations in the potential of the solution with maximum values of 1-2 mV. The applied gate voltage shown in the Figures corresponds to that maintained by a drain constant current of 100 µA and a drain-to-source constant voltage of 0.5 V. In this way, the variations in the transistor's threshold voltage are faithfully reflected in the applied gate voltage.

As shown in FIGS. 1a and 1b, the response of the REFET filled with hydrogel has high variations of potential in the order of 10 mV with significant variations in time, while in the case of the REFET without hydrogel it has lower variations of potential in the order of 2 mV and no significant variations in time.

There exists also, according to what is described in the document U.S. Pat. No. 4,874,499, a sensor with a configuration made up of a first ion sensor comprising an ion-sensitive membrane in the opening of a cavity in the first sensor, and a second sensor that acts as REFET with a porous membrane providing an opening in the cavity of the second sensor—the aim of this porous membrane is to allow a liquid junction between the inside and the outside of the cavity.

DESCRIPTION OF THE INVENTION

The present invention concerns an ion sensor based on differential measurement comprising:
- a substrate with at least one connecting track;
- one electrode linked to the substrate;
- a first ion-sensitive field-effect transistor (ISFET) with one gate, integrated in a first chip inserted in the substrate and linked to at least one connecting track;
- a second ion-sensitive field-effect transistor (ISFET) with one gate, integrated in a second chip inserted in the substrate and linked to at least one connecting track;
- a structure adhered on the first ion-sensitive field-effect transistor, configured to create a micro-reservoir on the gate of the first ISFET transistor;
- at least a first micro-channel connecting the micro-reservoir with the outside and allowing the renewal by diffusion of the reference solution; and
- an encapsulating material to isolate completely the connecting tracks and partially the first and the second ion-sensitive field-effect transistors.

More specifically, the micro-reservoir and the first micro-channel make up a unit totally or partially filled with a porous material, such as a mesoporous material or a macroporous material. This porous material forms a single body which covers entirely the gate of the first transistor and at least the base of the first micro-channel. This porous material has the capacity of absorbing a reference solution from the first micro-channel and spreading it to the gate of the first transistor, expelling or compressing the air inside the micro-reservoir and the first micro-channel.

In this way, the first ISFET transistor becomes a REFET transistor since its gate is in contact with the reference solution, and therefore its measurement remains constant and independent from the ion concentration in the solution to be measured. This solution to be measured is measured with the second ISFET. The response to the ion concentration of the potential of the electrode used to polarize the ISFET and REFET transistors does not interfere with the sensor's differential response because the measurement is performed in a differential way.

Optionally, the gate of the first ion-sensitive field-effect transistor (ISFET) is coated with a membrane which is sensitive to at least one type of ion. In this way, depending on the chosen membrane, the transistor will respond to a specific type of ion (for instance: lithium ion, calcium ion, potassium ion). These ISFETs coated with an ion-sensitive membrane are commonly known as CHEMFETs. An example is the PVC membrane containing valinomycin as ion-exchanger material, which is sensitive to potassium ($K^+$) ions, but there also exist membranes sensitive to other ions such as $Ca^{2+}$, $Na^+$, $Cl^-$, $NH_4^+$, $Li^+$.

Preferably, the micro-reservoir may be connected to the outside by a second micro-channel. This way, the micro-reservoir, the first micro-channel and the second micro-channel make up a unit totally or partially filled with a porous material, forming a single body which covers entirely the gate of the first transistor and at least the base of one of the micro-channels.

Preferably, the micro-reservoir and the first micro-channel are completely filled with a porous material, and the second micro-channel is totally or partially free of porous material to expel the air remaining inside the unit made up by the micro-reservoir and the micro-channel.

Optionally, the micro-reservoir and the first micro-channel are completely filled with a porous material, and the second micro-channel is empty, keeping the unit partially filled. In this way, when the sensor is put into the reference solution, this solution is absorbed by the first micro-channel and spread to the gate of the REFET transistor, expelling the air inside the first micro-channel and the micro-reservoir through the second micro-channel.

In a variation of the sensor based on differential measurement, the unit is an alternative unit which is made up only by the micro-reservoir and the first micro-channel; i.e. the micro-reservoir is not connected to the outside through a second micro-channel. This alternative unit is completely filled with porous material. In this way, when the sensor is immersed into the reference solution, this solution soaks the porous material generating a pressure inside the micro-reservoir that compresses air so that the micro-reservoir becomes partially filled with the solution. The layout of the REFET gate inside the micro-reservoir must be such that it remains in contact with the part filled with the reference solution. This configuration facilitates production.

In another aspect of the invention, it is described an ion measuring device comprising a container susceptible to be in contact with a medium for measuring its ion concentration. This container, in turn, comprises:
- the sensor previously described according to any of its variants,
- a control unit, linked to the abovementioned sensor, to calculate the ion concentration of the medium, and
- an indicator unit, linked to the control unit, to indicate visually the ion concentration of the medium to a user.

Preferably, the porous material occupies between 5% and 95% of the total volume of the unit made up by the micro-reservoir and the micro-channel or micro-channels, keeping the REFET transistor gate and at least the base of one of the micro-channels in contact with the porous material.

Preferably, this porous material has a pore size between 0.01 µm and 100 µm. More specifically, this porous material is the result of evaporating, inside the unit made up by the micro-reservoir and the micro-channel, an aqueous suspension containing 10% by weight of alumina particles the diameter of which ranges between 0.01 µm and 100 µm. When this suspension evaporates, it is generated the porous material with pores ranging between 0.01 µm and 100 µm that fills partially the abovementioned micro-reservoir and micro-channel.

Preferably, the porous material can be selected among, for example, alumina, silicon oxide, cellulose, polyamide, polystyrene. Preferably, the porous material is alumina.

Alternatively, the porous material comprises a number of pillars forming a single body as a kind of matrix. More specifically, these pillars have a diameter ranging between 0.01 µm and 100 µm, and are separated from each other by a distance ranging between 0.01 µm and 100 µm. Preferably, these pillars are made using micromachining techniques, for example, using photolithography processes with photosensitive materials.

Additionally, these pillars can be micromachined directly on the unit made up by the micro-reservoir and the micro-channel, so facilitating the production of the ion sensor.

This range in the pore size and/or in the separation between pillars prevents the generation of the Donnan potential, while ensuring a flow of reference solution by capillarity enough to expel the air inside the micro-reservoir and the micro-channel and to fill them partially with the reference solution in less than one minute.

Additionally, to make possible the absorption of the reference solution by capillarity, the porous material must be hydrophilic, i.e. it must have a contact angle lower than 90°. If the porous material does not have a contact angle lower than 90°, in that case it can be obtained by means of some known treatment, such as activating the surfaces of the porous material in oxygen plasma, and/or coating these surfaces with molecules containing ionizable functional groups in aqueous solution, for example, 3-aminopropyl triethoxysilane.

This porous and hydrophilic material, unlike other porous materials with smaller pore sizes, prevent the formation of the Donnan potential, and therefore it presents no potential difference between the inside of the pores and the solution to be measured into which the sensor is immersed during the measurement performance. So, even existing a liquid junction between the reference solution and the solution to be measured, the errors in the measurement are not greater than those obtained with a REFET that has all the volume inside the micro-reservoir and the micro-channel filled solely with reference solution. In this way, due to its hydrophilic properties, it allows the micro-reservoir to fill partially or totally with the reference solution quickly. Therefore, it presents a more accurate measurement than the ISFET-REFET sensor the micro-reservoir of which is filled with gel.

Another advantage of this invention is due to the fact that the porous material is highly hydrophilic, and so it takes longer, compared with the REFET filled solely with reference solution, to dry out if the sensor is left out of the reference solution.

Additionally, in the event that it dries out completely, it can be easily and quickly rehydrated by immersing it again into the reference solution, without risk of bubble formation, hence its useful life is longer in comparison with the sensors described in the state of the art. This sensor also allows being immersed into the reference solution to recalibrate the sensor and to return the ion concentration in the micro-reservoir and the microchannel, or micro-channels, to its level prior to the performance of the measurements.

Another advantage of the present invention is the fact that, unlike the sensors with porous membranes to create the liquid junction between the inside and the outside of the micro-reservoir, as the document U.S. Pat. No. 4,874,499 expounds, the sensor of the present invention allows an easier filling of the micro-reservoir, since by simply immersing the sensor into the reference solution, it flows by capillarity and fills partially or totally the reservoir. A porous membrane like the one described in the aforementioned document is not in contact with the gate of the second sensor and does not fill partially nor totally the micro-reservoir of the second reference sensor. The document U.S. Pat. No. 4,874,499 mentions the need of additional micro-channels to fill the sensor. In this case, the filling does not occur by capillarity, and an active system is needed to pump the reference solution into the micro-reservoir.

In summary, thanks to this characteristic configuration, this sensor presents no relevant interferences in the ion concentration measurement, presents no air bubble formation in the REFET gate, can be rehydrated quickly, and has a longer useful life.

DESCRIPTION OF THE DRAWINGS

In order to supplement the description now being given, and with the aim of contributing to a better understanding of the characteristics of the invention according to a preferred practical embodiment, the present description is accompanied, as an integral part thereof, by a set of drawings provided for illustrative non-limiting purposes, in which.

PREFERRED EMBODIMENT OF THE INVENTION

Figure 2:
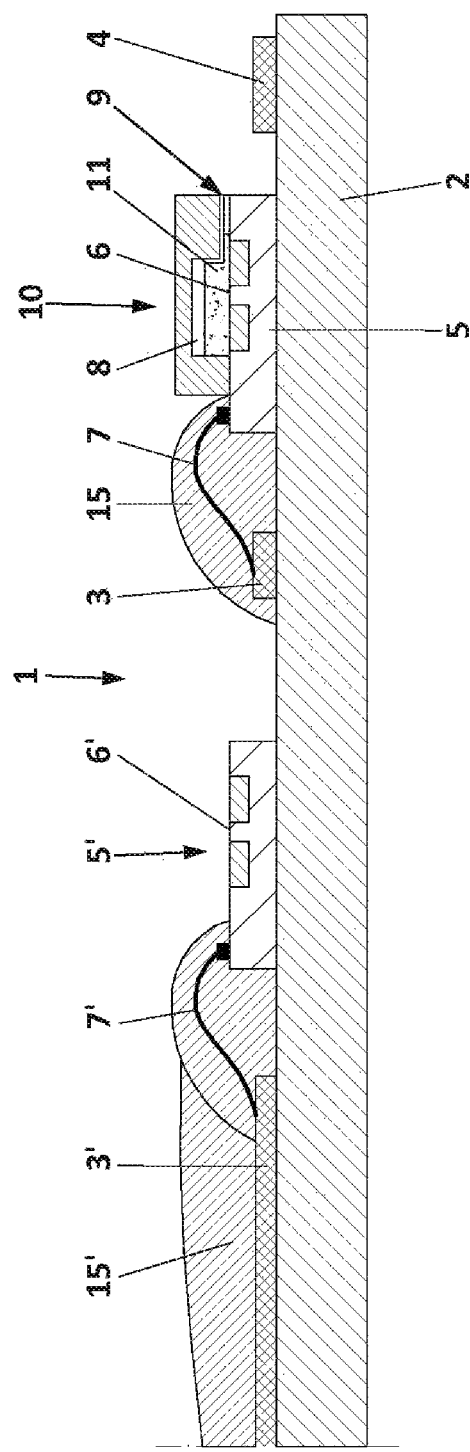
FIG. 2 shows a schematic view of the ion sensor based on differential measurement.

In a preferred embodiment of the invention, as shown in FIG. 2, the ion sensor (1) based on differential measurement consists of a substrate (2) with connecting tracks (3, 3') and one electrode (4).

On the aforementioned substrate (2) there are integrated a first and a second ion-sensitive field-effect transistor with one gate which are integrated in a first and a second chip, known as ISFET transistors (5, 5') with their respective gates (6, 6'), being both connected to the connecting tracks (3, 3') by means of bondable wires (7, 7'). More specifically, the first ISFET transistor (5) is covered by a structure forming a micro-reservoir (8) on its gate (6) and is connected to the outside by a micro-channel (9). With this configuration of the ISFET (5), the micro-reservoir (8) and the micro-channel (9) make up a REFET transistor (10) which measures a reference solution (12), while the other ISFET transistor (5') measures a solution to be measured. The sensor (1) compares the potential difference between both measurements to know the ion concentration in the solution to be measured.

Additionally, the sensor (1) comprises a polymeric encapsulating material (15, 15') covering completely the aforementioned connecting tracks (3, 3') and the wires (7, 7'). This encapsulating material (15') covers partially the ISFET transistor (5'), keeping its gate (6') uncovered. With regard to the REFET transistor (10), the encapsulating material (15) only covers the area where the bondable wire (7) is linked to the REFET transistor (10).

Figure 3:
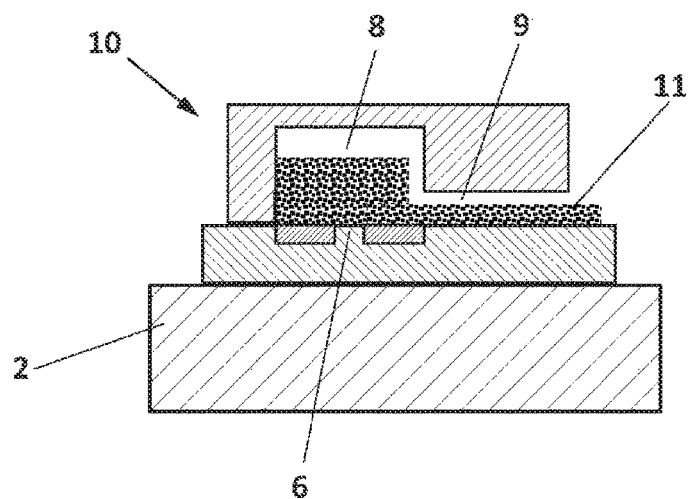
FIG. 3 shows a schematic view of the preferred configuration of the REFET.

FIG. 3 shows in greater detail the REFET transistor (10); in particular the micro-reservoir (8) and the micro-channel (9) make up a unit partially filled with a porous material (11). This porous material (11) forms a single body which covers entirely the gate (6) of the ISFET transistor (5) and the base of the micro-channel (9). This porous material (11) comprises alumina particles forming a number of pores with a diameter of 0.05 μm. Additionally, the porous material (11) occupies 10% of the total volume of the unit made up by the micro-reservoir (8) and the micro-channel (9).

Figure 4:
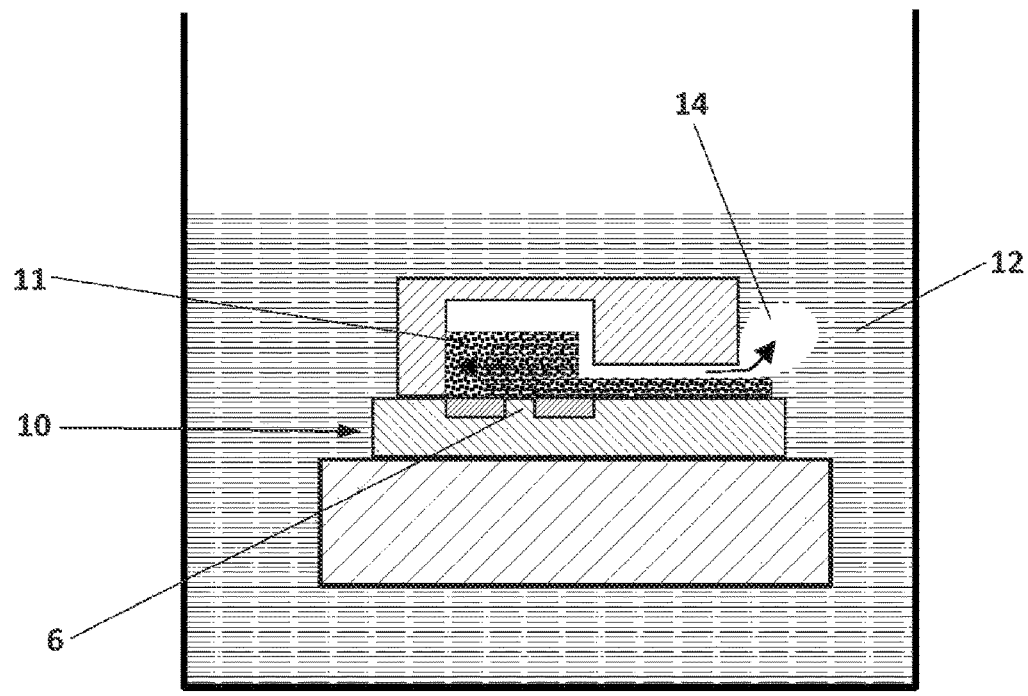
FIG. 4 shows a schematic view of the REFET in the previous figure immersed into the reference solution.

Thanks to this configuration, as FIG. 4 shows schematically, when the sensor (1) is immersed into the reference solution (12), the porous material (11) absorbs the reference solution (12) by capillarity through the micro-channel (9) and spreads it to the gate (6) that forms part of the REFET (10). Instantaneously, due to the pressure exerted by the effect of capillarity, the air (14) occupying the unit of the micro-reservoir (8) and the micro-channel (9) is expelled through the zone free of porous material (11).

Figure 5:
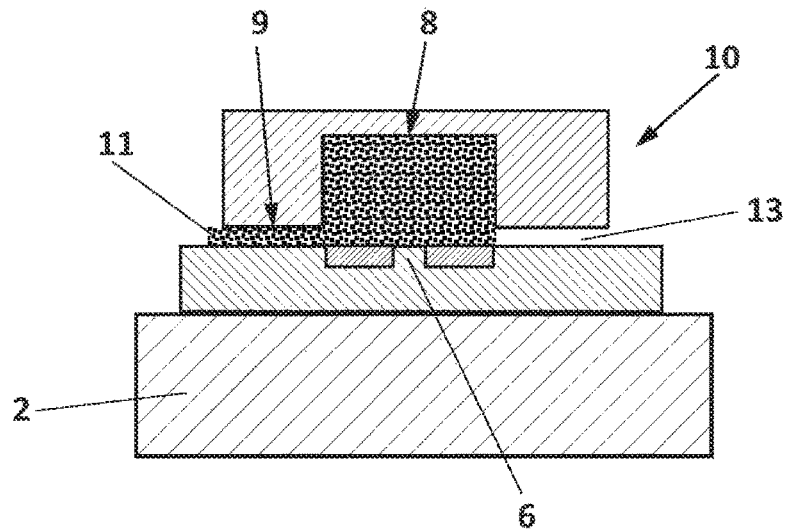
FIG. 5 shows a schematic view of another preferred configuration of the REFET.

In another preferred embodiment, shown in FIG. 5, the micro-reservoir (8) incorporates an additional micro-channel (13) to allow the exit of the air (14) that accumulates inside the micro-reservoir (8). Specifically, the micro-reservoir (8) and the micro-channels (9, 13) make up a unit partially filled with the porous material (11) forming a single body. The porous material occupies the entirety of the micro-reservoir (8) and the first micro-channel (9) and leaves exposed the entirety of the second micro-channel (13).

Figure 6:
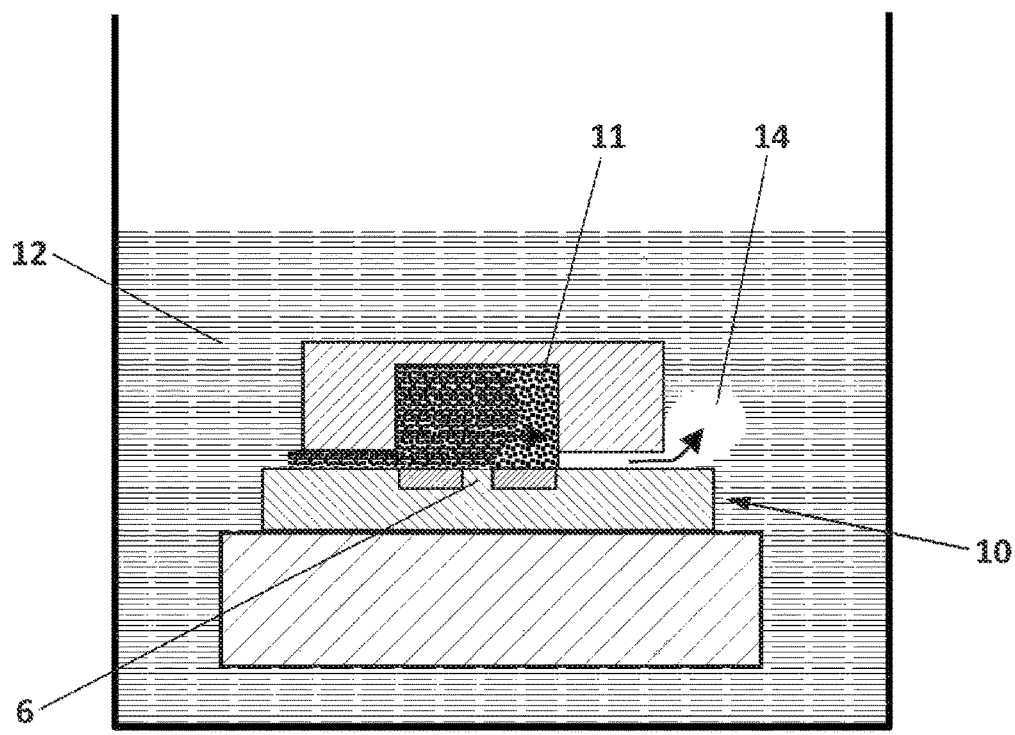
FIG. 6 shows a schematic view of the REFET in the previous figure immersed into the reference solution.

In this way, as FIG. 6 shows, when the sensor (1) is immersed into a reference solution (12), the porous material (11) absorbs the reference solution (12) by capillarity through the micro-channel (9) and spreads it to the gate (6) of the REFET (10). Instantaneously, the air (14) occupying the unit of the micro-reservoir (8) and the first micro-channel (9) is expelled through the second micro-channel (13), i.e. the zone free of porous material (11).

Figure 7:
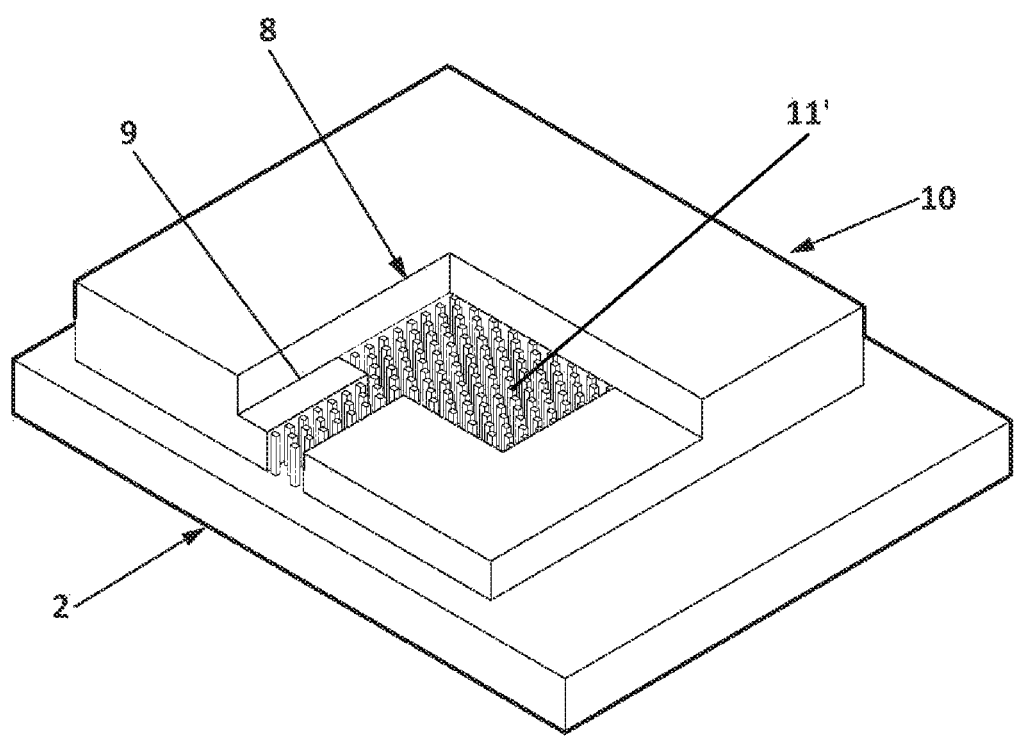
FIG. 7 shows a schematic view of another preferred configuration of the REFET, with a partial cut-away showing the inside of the micro-reservoir.

In another preferred embodiment of the invention, shown in FIG. 7, the porous material (11') comprises a number of pillars forming a single body as a kind of matrix on the unit made up by the micro-reservoir (8) and the micro-channel (9). These pillars have been micromachined using lithography directly on the structure of the micro-reservoir (8), have a diameter of 10 μm, and are separated from each other by a distance of 10 μm.

Figure 1:
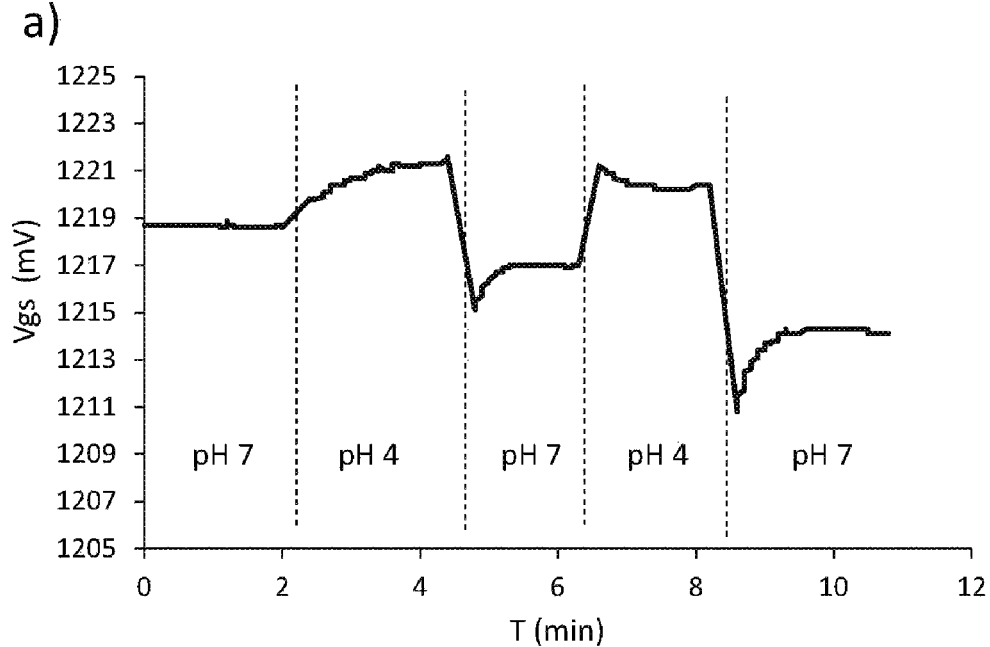
FIG. 1a shows a chart of the results obtained from the measurement with a REFET filled with poly(HEMA)-type gel, according to a solution known in the state of the art.
FIG. 1b shows a chart of the results obtained from the measurement with a REFET filled with the reference solution, according to a solution known in the state of the art.
Figure 1:
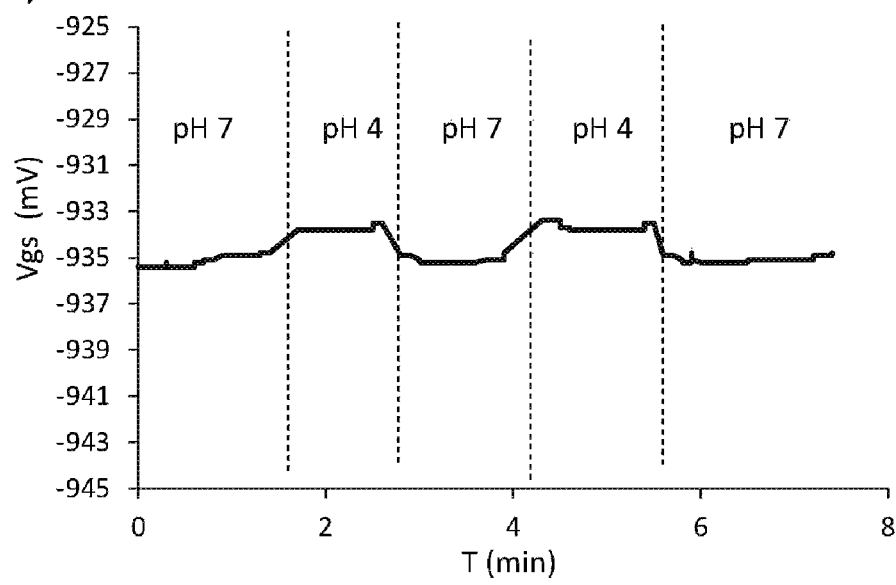
Figure 8:
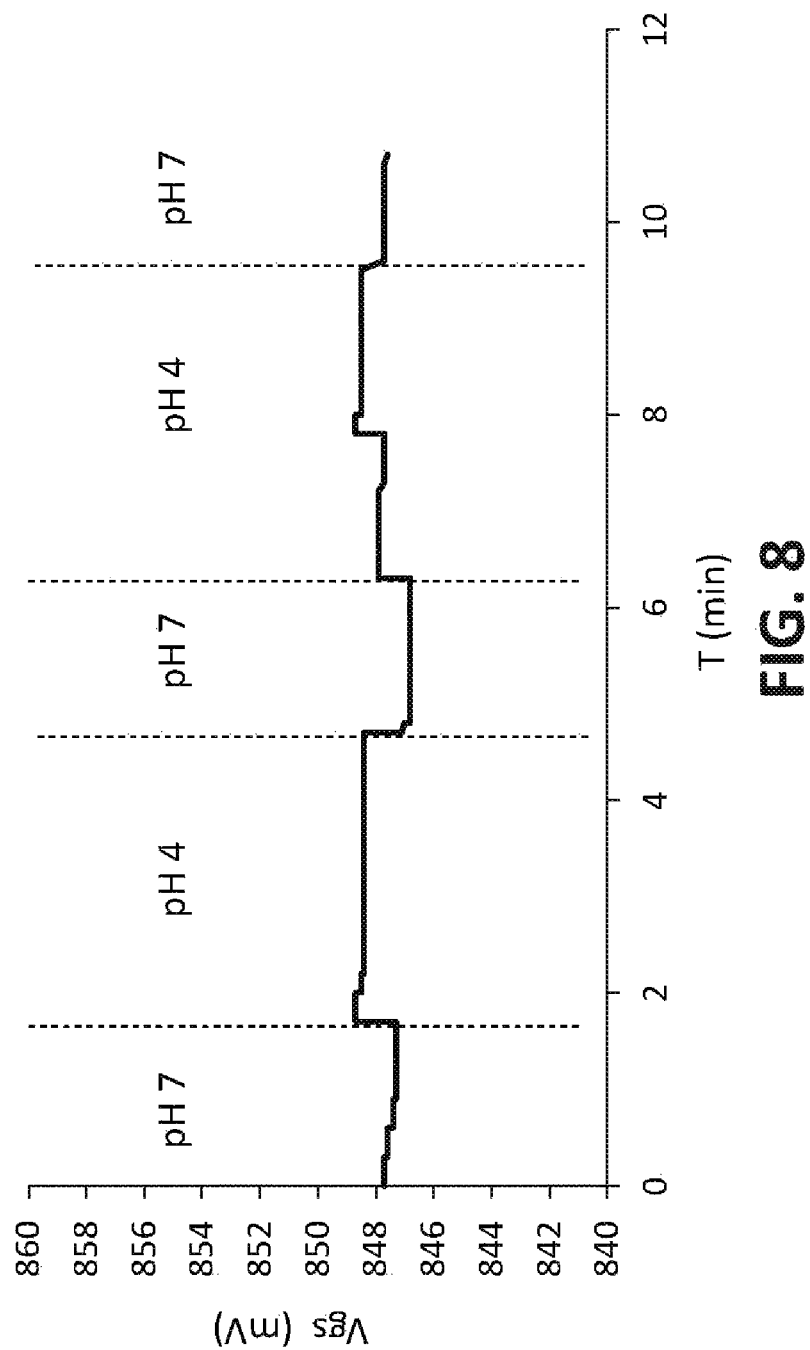
FIG. 8 shows a chart of the results obtained from the measurement with a REFET filled with a porous material.

With the purpose of demonstration the advantages of the sensor (1), several tests have been carried out. In particular, tests have been made with configurations of micro-reservoir (8) with one micro-channel (9) as the one in FIG. 3; two micro-channels (9, 13) as the one represented in FIG. 5; or with a matrix of pillars as the one in FIG. 7, obtaining the results displayed in FIG. 8. Comparing the FIGS. 1a, 1b and 8, it can be observed graphically the improvements of the present invention over the state of the art. In this way, the sensor (1) of the present invention presents no interferences in the measurements, which are common in other sensors with gels, and the contribution of the REFET to its response to different pHs is small and stable, comparable to the case of using directly the reference solution (12).

Figure 9:
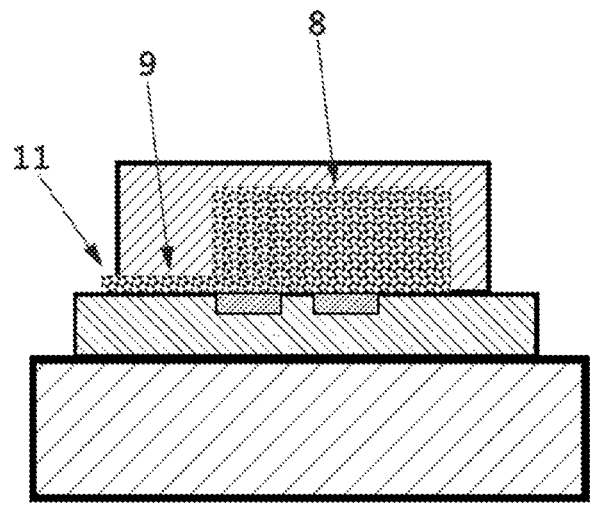
FIG. 9 shows a schematic view of another preferred configuration of the REFET.

In another preferred embodiment of the sensor (1), as shown in FIG. 9, the micro-reservoir (8) and the first micro-channel (9) are totally filled with porous material (11) and there is no second micro-channel.

Figure 10:
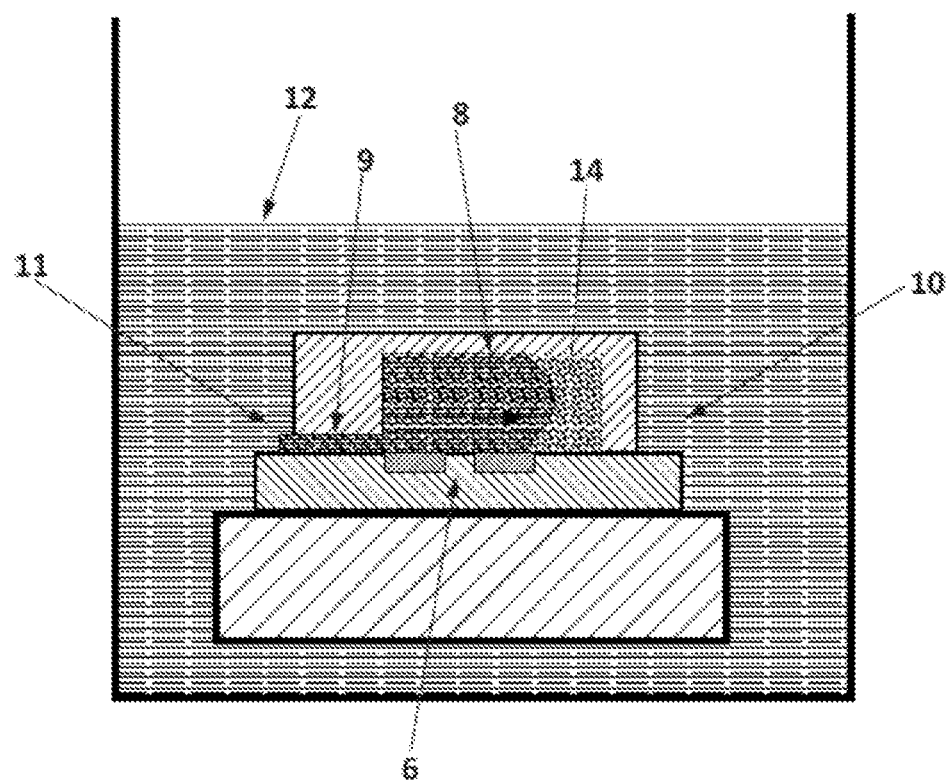
FIG. 10 shows a schematic view of the REFET in FIG. 9 immersed into the reference solution.

In this way, as FIG. 10 shows, when the sensor (1) is immersed into a reference solution (12), the porous material (11) absorbs the reference solution (12) by capillarity through the micro-channel (9) and spreads it to the gate (6) of the REFET (10). Instantaneously, the air (14) occupying the unit of the micro-reservoir (8) and the first micro-channel (9) is compressed inside the micro-reservoir (8).

The invention claimed is:

1. An ion sensor (1) based on differential measurement comprising:
   a substrate (2) with connecting tracks (3, 3');
   an electrode (4);
   a first ion-sensitive field-effect transistor (5) with one gate (6), integrated in a first chip inserted in the substrate (2) and linked to at least one connecting track (3) of the connecting tracks (3, 3');
   a second ion-sensitive field-effect transistor (5') with one gate (6'), integrated in a second chip inserted in the substrate (2) and linked to at least one connecting track (3') of the connecting tracks (3, 3');
   a structure adhered on the first ion-sensitive field-effect transistor (5) configured to create a micro-reservoir (8) on the gate (6) of the first ion-sensitive field-effect transistor (5);
   a first micro-channel (9) connecting the micro-reservoir (8) with an outside; and an encapsulating material (15, 15') to isolate completely the connecting tracks (3, 3') and partially the first and the second ion-sensitive field-effect transistors (5, 5'), wherein the micro-reservoir (8) and the first micro-channel (9) make up a first unit totally or partially filled with a porous material (11), said porous material (11) forming a first single body which covers entirely the gate (6) of the first ion-sensitive field-effect transistor (5) and at least a base of the first micro-channel (9), and configured to absorb a reference solution (12) from the outside through the first micro-channel (9) to the gate (6) of the first ion-sensitive field-effect transistor (5), expelling or compressing an air (14) inside the first unit.

2. The ion sensor (1) according to claim 1, wherein the micro-reservoir (8) is connected to the outside by a second micro-channel (13).

3. The ion sensor (1) according to claim 2, wherein the micro-reservoir (8), the first micro-channel (9) and the second micro-channel (13) make up a second unit totally or partially filled with the porous material (11), said porous material (11) forming a second single body which covers entirely the gate (6) of the first ion-sensitive field-effect transistor (5) and at least the base of the first micro-channel (9).

4. The ion sensor (1) according to claim 3, wherein the first unit is completely filled with the porous material (11) and the second micro-channel (13) is totally or partially free of the porous material (11) to expel the air (14) remaining inside the first unit.

5. The ion sensor (1) according to claim 3, wherein the porous material (11) fills between 5% and 95% of the total volume of the second unit.

6. The ion sensor (1) according to claim 1, wherein the porous material (11) fills between 5% and 95% of the total volume of the first unit.

7. The ion sensor (1) according to claim 1, wherein the porous material (11) has pores with a diameter ranging between 0,01 µm and 100 µm.

8. The ion sensor (1) according to claim 1, wherein the porous material (11) comprises a number of pillars forming the first single body as a matrix, where each pillar has a diameter ranging between 0,01 µm and 100 µm, and said each pillar is separated from its contiguous said number of pillars by a distance ranging between 0,01 µm and 100 µm.

9. The ion sensor (1) according to claim 1, wherein the first unit is totally filled with the porous material (11).

10. An ion measuring device comprising a container susceptible to be in contact with a medium for measuring its ion concentration, wherein the container comprises:
the ion sensor (1) according to any of the previous claims,
a control unit, linked to the above mentioned ion sensor (1) based on differential measurement, to calculate the ion concentration of the medium, and
an indicator unit, linked to the control unit, to indicate visually the ion concentration of the medium.

* * * * *